(12) United States Patent
Colantonio

(10) Patent No.: US 9,987,435 B2
(45) Date of Patent: Jun. 5, 2018

(54) APPARATUS AND METHOD FOR SAFELY INSERTING AN INTRODUCER NEEDLE INTO EPIDURAL SPACE

(76) Inventor: Anthony J. Colantonio, Meadville, PA (US)

( * ) Notice: Subject to any disclaimer, the term of this patent is extended or adjusted under 35 U.S.C. 154(b) by 945 days.

(21) Appl. No.: 13/261,532

(22) PCT Filed: Jun. 8, 2011

(86) PCT No.: PCT/US2011/001035
§ 371 (c)(1),
(2), (4) Date: Dec. 4, 2012

(87) PCT Pub. No.: WO2011/155988
PCT Pub. Date: Dec. 15, 2011

(65) Prior Publication Data
US 2013/0072900 A1 Mar. 21, 2013

Related U.S. Application Data

(60) Provisional application No. 61/397,304, filed on Jun. 10, 2010.

(51) Int. Cl.
*A61M 5/32* (2006.01)
*A61B 17/34* (2006.01)
*A61B 17/00* (2006.01)

(52) U.S. Cl.
CPC ........... *A61M 5/32* (2013.01); *A61B 17/3401* (2013.01); *A61B 17/3496* (2013.01); *A61B 2017/00477* (2013.01)

(58) Field of Classification Search
CPC ........ A61M 5/284; A61M 5/178; A61M 5/34; A61M 5/41; A61B 18/04
See application file for complete search history.

(56) References Cited

U.S. PATENT DOCUMENTS 4,141,365 A * 2/1979 Fischell ............... A61N 1/0551
600/377
5,031,634 A * 7/1991 Simon ................ A61B 17/3403
600/567
5,846,226 A * 12/1998 Urmey ............... A61B 17/3401
604/158

(Continued)

*Primary Examiner* — Bhisma Mehta
*Assistant Examiner* — Matthew A Engel
(74) *Attorney, Agent, or Firm* — Carothers & Carothers

(57) ABSTRACT

An epidural needle assembly is provided, permitting the accurate introduction of a large bore introducer sleeve needle into the epidural space in the spinal column of a patient using the loss of resistance technique. The large bore introducer needle has a beveled side opening at its tip and with a tissue piercing point at the distal extension of the needle. A syringe needle is received within the introducer needle with a distal head of the syringe needle filling the beveled side opening at the distal end of the introducer needle when the syringe hub is fully seated. The lumen of the syringe needle exits the syringe needle head at the side opening of the introducer needle immediately adjacent the tissue piercing point of the introducing needle. The needle assembly may be inserted and advanced, with precise tactile feedback, into a patient, thus accurately detecting the introduction of the introducer needle into epidural space.

16 Claims, 10 Drawing Sheets

(56) References Cited

U.S. PATENT DOCUMENTS

| | | | | |
|---|---|---|---|---|
| 5,919,172 | A * | 7/1999 | Golba, Jr. | A61B 17/3401 604/164.01 |
| 7,553,307 | B2 * | 6/2009 | Bleich | A61B 17/1671 606/1 |
| 7,555,343 | B2 * | 6/2009 | Bleich | A61B 90/04 600/554 |
| 2005/0267527 | A1 * | 12/2005 | Sandoval | A61B 17/0057 606/213 |
| 2006/0122458 | A1 * | 6/2006 | Bleich | A61B 17/1659 600/101 |
| 2008/0071281 | A1 * | 3/2008 | Wilson | A61M 5/46 606/92 |

* cited by examiner

APPARATUS AND METHOD FOR SAFELY INSERTING AN INTRODUCER NEEDLE INTO EPIDURAL SPACE

CROSS REFERENCE

Applicant claims the benefit of earlier filed Provisional Patent Application No. 61/397,304, filed on 10 Jun. 2010.

FIELD OF THE INVENTION

The present invention relates generally to the field of hyperdermic needles, and more particularly to an epidural needle assembly for safely introducing a introducer needle into the epidural space in the spinal column of a patient.

BACKGROUND OF THE INVENTION

Traditionally, actually for centuries, needle access to the epidural space around the spine has been achieved with a technique known as "loss of resistance". During this technique, the operator will normally use a small gauge (18G to 14G, and more typically, 18G or 17G) needle and a syringe of saline or air attached to the hub of the needle. The needle is advanced through the skin and underlying tissue until it engages the ligament layers over the spine and epidural space. As the needle is advanced through the soft tissue underlying the skin, the operator exerts constant pressure on the plunger of the syringe, which is attached to the hub of the needle. When the needle is within ligament, there is considerable resistance on the plunger. However, when the needle passes into the epidural space, the resistance is gone or lost and the plunger advances easily at this point thereby informing the operator through tactile response that the tip of the needle has been introduced into the epidural space.

Physicians are trained to use typically 17 and 18 gauge needles in most instances. Accordingly, the tactile response with needles of this gauge is very familiar to the operator. For best clinical practice, this precise tactile feedback should be maintained to optimize the chances of properly identifying the epidural space.

It is also common practice to introduce large bore sleeve needles generally referred to as introducer needles into the epidural space for introduction of larger elements, such as paddle, flat or wire leads, into the epidural space. For example, see U.S. Pat. Nos. 7,022,109; 6,553,264; 6,309,401; 6,249,707; 6,245,044; 5,669,882 and 5,255,691.

The gauge of such introducer sleeve needles exceeds that which is familiar to the operator, and accordingly, use of the loss of resistance technique is impossible when introducing the tip of such an introducer sleeve needle into the epidural space.

The gauge of such introducer sleeve needles is not always specified, and for example, in U.S. Pat. No. 6,309,401 it is based on size of the paddle leads to be inserted through the introducer needle, and therefore would need to be 10 gauge or larger.

In the prior art, the method normally used to introduce such an introducer sleeve needle into epidural space is to attach a syringe to the large oblong introducer hub, and attempt to use the loss of resistance technique. However, in this case, the precision of the tactile feedback from such a large bore needle is lost and this provides a significant negative impact on the success rate of the procedure for introducing an introducer sleeve needle into the epidural space.

Other problems are also incurred. With respect to the introducer sleeve needle disclosed in U.S. Pat. No. 6,309,401, a hub is fixed to the body of the introducer needle and cannot be removed. In order to pass paddle leads through the introducer sleeve needle, the leads would have to pass through the hub at some point. The hub would either be too small to pass the paddle leads, or it would have to be as large an opening as the diameter of the oblong introducer to fit the paddle leads therethrough. In the first instance, the operator would not be able to pass the leads through the device. In the latter case, the operator would never find a syringe with the proper fitting to mate with the hub to even attempt a loss of resistance technique. Furthermore, in the latter instance, there would be a complete loss of tactile feedback to the operator as the introducer sleeve needle is advanced making it extremely risky and difficult to identify the epidural space.

It is a principal object of the present invention to eliminate these aforementioned risks and shortcomings, and to provide an epidural needle assembly for safely introducing a large bore introducer sleeve needle into the epidural space of the spinal column of a patient and for inserting wide lead elements, or multiples thereof, into the epidural space. The invention also uniquely provides for the simultaneous introduction of multiples of lead elements into the epidural space or other subcutaneous tissue layer.

SUMMARY OF THE INVENTION

The present invention provides an introducer epidural needle assembly for safely achieving access to the epidural space, which includes an elongated large bore introducer sleeve needle having a beveled side opening at its distal tip which provides a tissue piercing point at the distal tip. A large diameter lumen extends fully through the introducer sleeve needle. The combination further includes a syringe needle that is removable insertable within the lumen of the introducer sleeve needle and the syringe needle is provided with a syringe hub at its proximal end and a head at its distal end. The syringe needle head is dimensioned and contoured to fill the beveled side opening at the distal end of the introducer sleeve needle when the hub of the syringe needle is fully seated on the proximal end of the introducer sleeve needle. The syringe needle head thus seated provides a syringe needle lumen exit of a predetermined gauge which exits the syringe needle head immediately adjacent the flesh piercing point of the introducer sleeve needle. This epidural needle assembly uniquely permits the loss of resistance technique to be employed when introducing the introducer sleeve needle into the epidural space. Such precise introduction and positioning of the introducer sleeve needle was not previously possible with the needle assemblies of the prior art.

The method or procedure of the present invention is carried out by filling the beveled side opening of the introducer sleeve needle with the head of the syringe needle by inserting the syringe needle into the lumen of the introducer sleeve needle until the hub of the syringe needle is fully seated on the distal end of the introducer sleeve needle. Then, the lumen exit of the syringe needle on the head of the syringe needle is plugged by inserting a solid stylet into the lumen of the syringe needle to thereby block the entry of debris into the syringe lumen exit, thereby completing the assembly.

Then the needle assembly is manipulated to percutaneously insert the point of the introducer sleeve needle into skin of the patient at a desired spinal area. Thereafter the stylet is removed from the syringe needle lumen and a plunger actuated syringe containing non-toxic fluid, such as saline solution or air, is secured to the syringe hub of the syringe needle. The assembly is thus further advanced through soft tissue layers underlying the skin toward the epidural space while applying plunger ejection pressure to the syringe, thereby ejecting the non-toxic fluid under pressure from the syringe needle lumen exit immediately adjacent to the introducer sleeve needle point. This permits detecting the entry of the point of the introducer sleeve needle into the epidural space with precise tactile feedback to the plunger of the syringe. Thereafter the syringe needle may be removed from the introducer needle lumen whereby the introducer sleeve needle remains positioned in the epidural space for future use.

The syringe needle hub is keyed with the proximal end of the introducer needle when they are fully seated to each other to prevent relative rotation. In a similar fashion, the stylet is also keyed against rotation relative to the syringe needle when fully seated together to plug the syringe needle lumen exit.

In an alternative embodiment, the introducer sleeve needle is provided with a longitudinal side slot that extends the full length of the introducer sleeve needle. The syringe needle further includes a longitudinal wing rib which extends through this side slot for a predetermined lateral distance beyond the slot, whereby a tissue path made by the introducer sleeve needle in tissue is dilated and thereby widened for later introduction of wide lead elements through the introducer sleeve needle and into the epidural space. Accordingly, exceptionally wide lead elements, such as paddle, flat or wire leads, may be introduced into the epidural space through the introducer sleeve needle with portions of the wide lead protruding through the side slot of the introducer sleeve needle as the wide lead is progressing through the introducer sleeve needle.

The introducer sleeve needle preferably includes depth markings on the exterior surfaces thereof for assessing the depth of penetration. Typically such markings are in centimeter increments.

BRIEF DESCRIPTION OF THE DRAWINGS

Other objects and advantages appear hereinafter in the following description and claims. The accompanying drawings show, for the purpose of exemplification, without limiting the scope of the invention or appended claims, certain practical embodiments of the present invention wherein:

DETAILED DESCRIPTION OF THE PREFERRED EMBODIMENT

Figure 1:
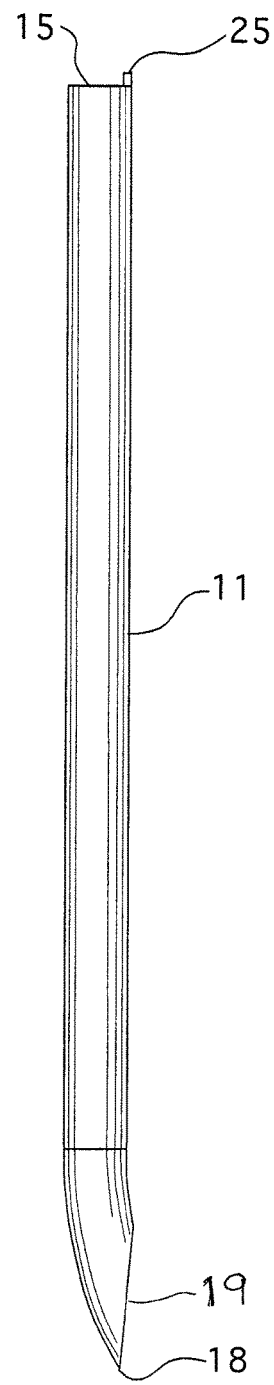
FIG. 1 is a view in side elevation of a large bore circular introducer sleeve needle utilized in the epidural needle assembly of the present invention.
Figure 2:
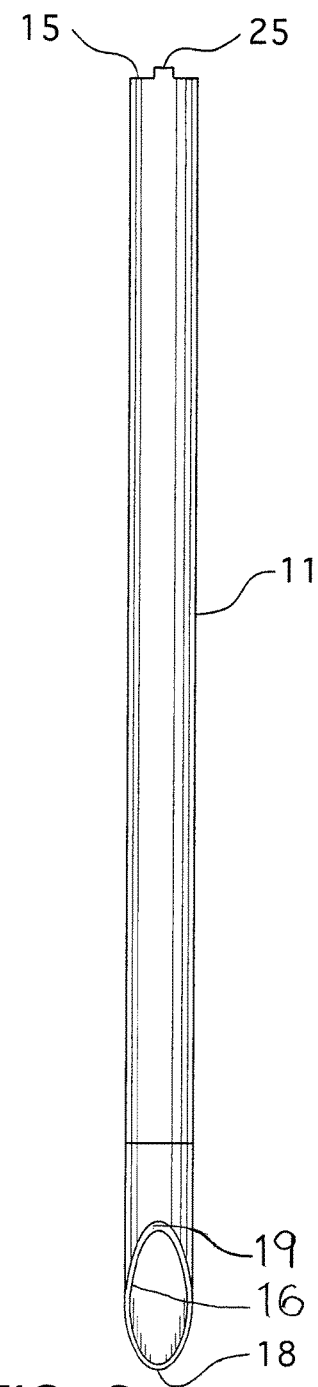
FIG. 2 is a view in front elevation of the introducer sleeve needle shown in FIG. 1.

Referring to FIGS. 1 through 6, the epidural needle assembly 10 of the present invention is comprised, at a minimum, of the combination of large bore introducer sleeve needle 11 and syringe needle 12. Elongated tubular introducer sleeve needle 11 is provided with a lumen 13 extending from its distal tip 14 to its proximal end 15, with a beveled side opening 16 at its distal end. Introducer sleeve needle 11 is also provided with a curved distal tip 17 having a flesh or tissue piercing point 18 at its distal tip.

Introducer sleeve needle 11 is a large bore needle which is provided to allow the insertion of larger objects, such as a paddle lead, flat lead or a wire lead, into the epidural space after the tip 14 has been inserted into the epidural space. All components shown are constructed of surgical stainless steel or an equivalent thereof.

Syringe needle 12 is provided at its proximal end 15 with a conventional hub 20 for connecting a conventional plunger actuated syringe (not shown) thereto in conventional fashion. The internal lumen 21 of syringe needle 12 is of predetermined cross section, most typically gauge 18 or 17, and continuously extends through syringe needle 12. An enlarged head 22 is secured to the distal end of syringe needle 12. Syringe needle 12 is dimensioned and contoured to receive in lumen 13 of introducer sleeve needle 11 with the hub 20 releasably seated with the proximal end 15 of introducer sleeve needle 11, and the head 22 filling the beveled side opening 16 when hub 20 is fully seated to the proximal end 15 of introducer sleeve needle 11 as illustrated in FIG. 6.

Figure 6:
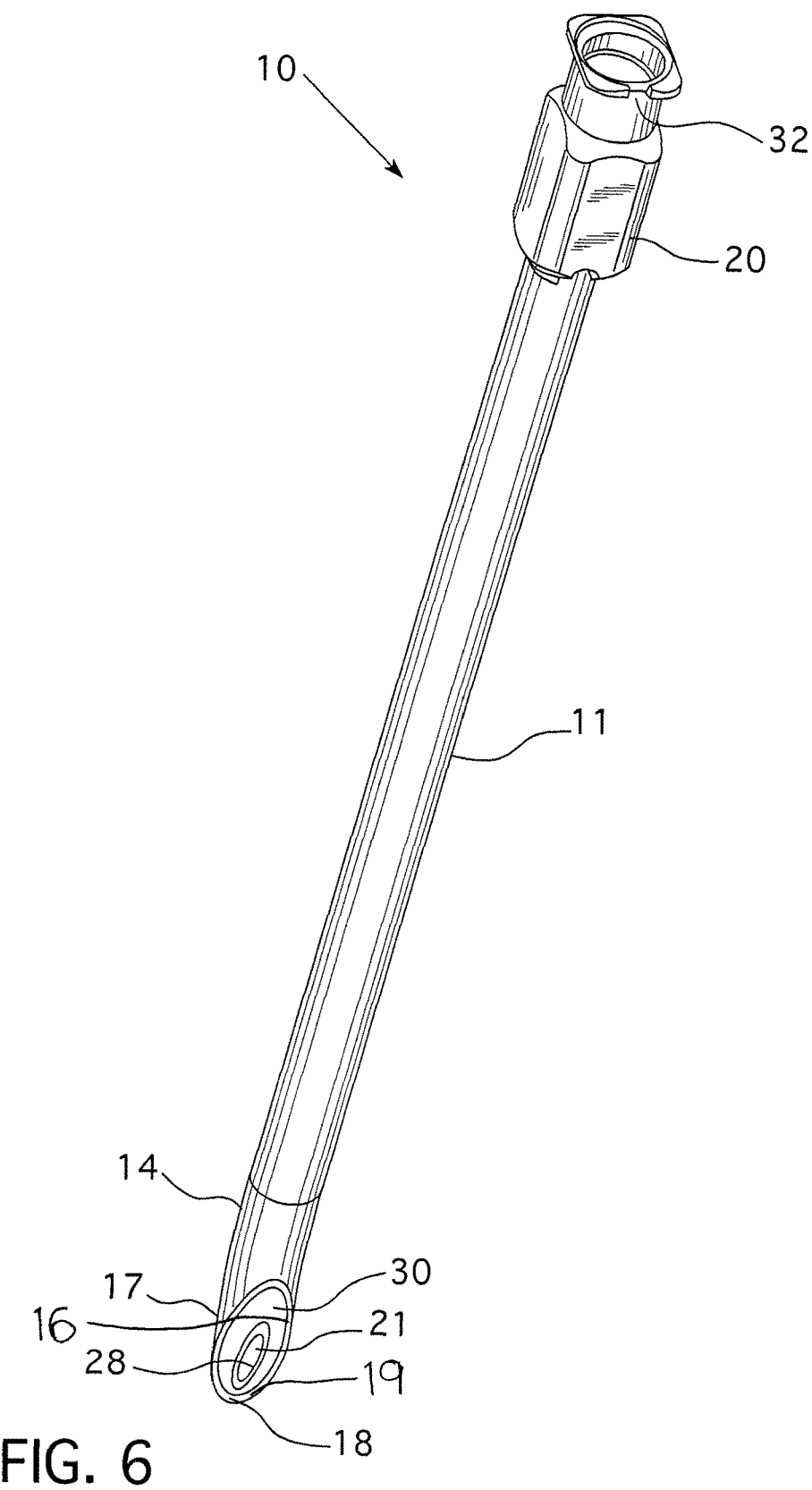
FIG. 6 is a perspective view showing the introducer sleeve needle of FIG. 1, 2 or 5 in combination with the syringe needle of FIG. 3, 4 or 5 without the inclusion of the stylet shown in FIG. 5.
Figure 9:
FIG. 9 is a top end view of the introducer sleeve needle shown in FIG. 8.
Figure 7:
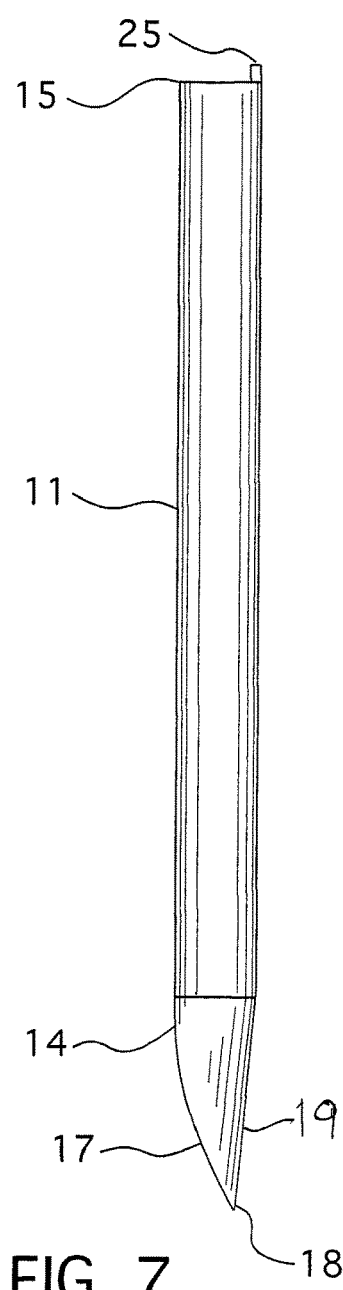
FIG. 7 is a view in side elevation showing another embodiment of an introducer sleeve needle with an oblong bore used in the epidural needle assembly of the present invention.
Figure 8:
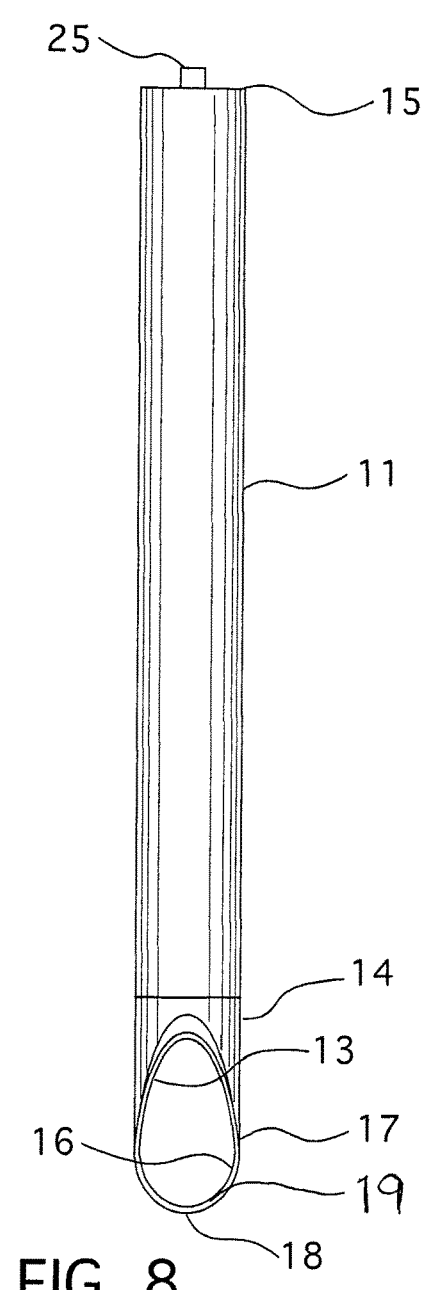
FIG. 8 is a view in front elevation of the introducer sleeve needle shown in FIG. 7.
Figures 10, 11:
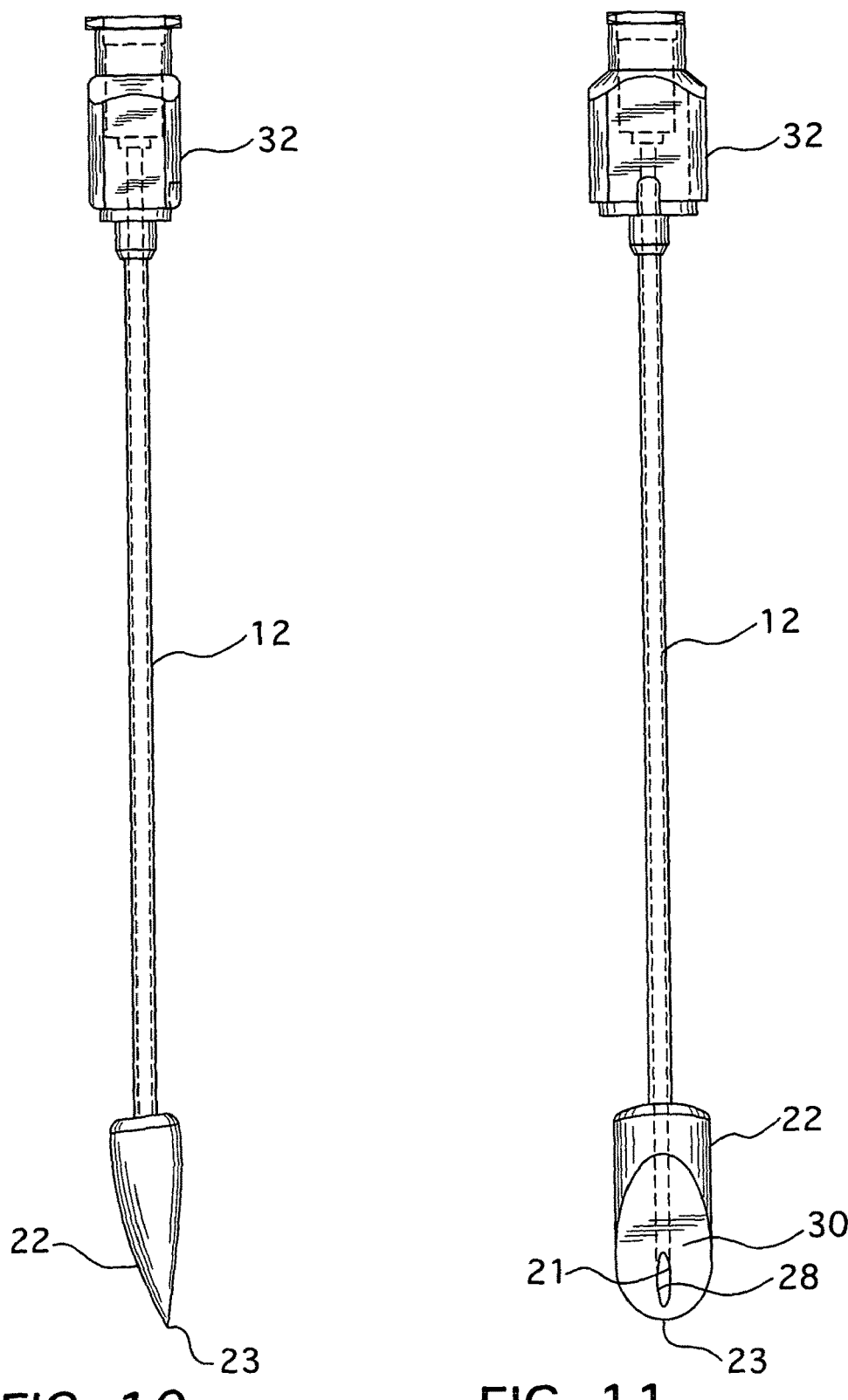
FIG. 10 is a view in side elevation of another embodiment of a syringe needle to be used in combination with the introducer needle embodiment shown in FIG. 7.
FIG. 11 is a view in front elevation of the syringe needle shown in FIG. 10.
Figure 12:
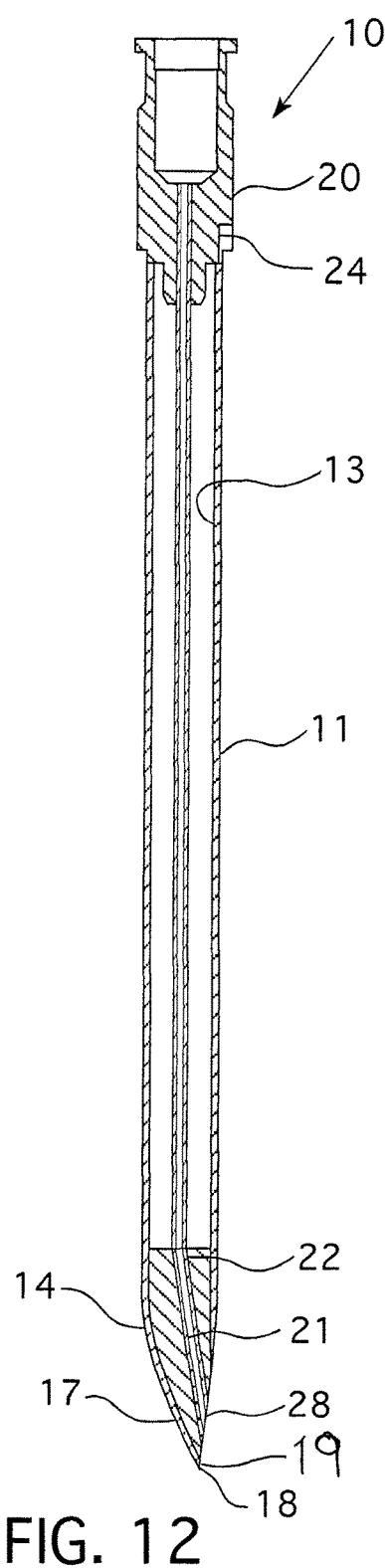
FIG. 12 is a view in side elevation and in vertical mid cross section of the introducer sleeve needle shown in FIGS. 7, 8 and 9 in combination with the syringe needle of FIGS. 10 and 11.
Figure 13:
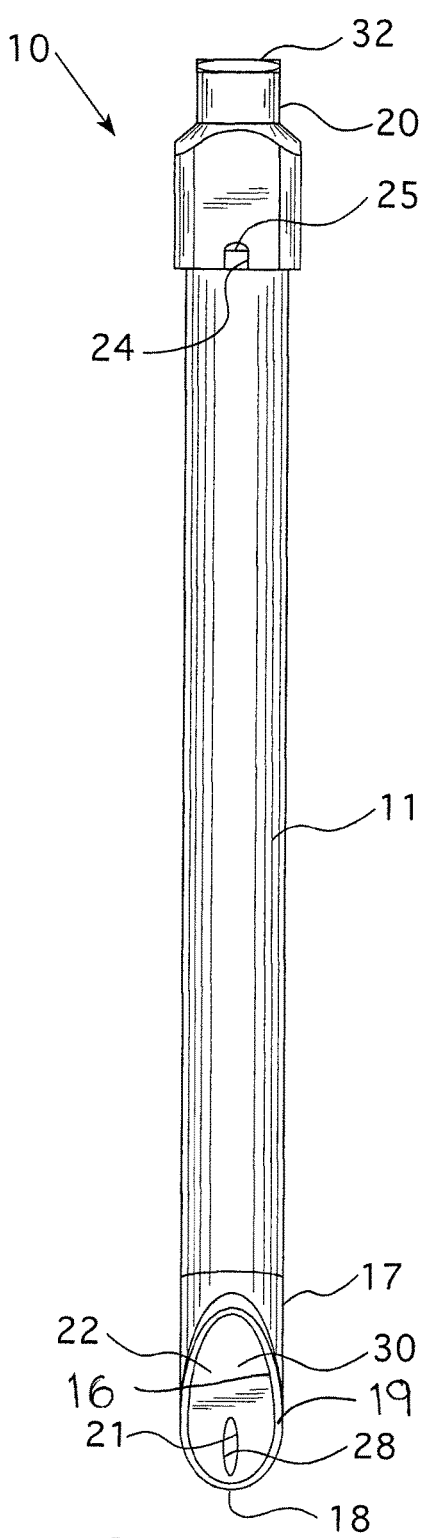
FIG. 13 is a view in front elevation of the combination shown in FIG. 12.
Figure 14:
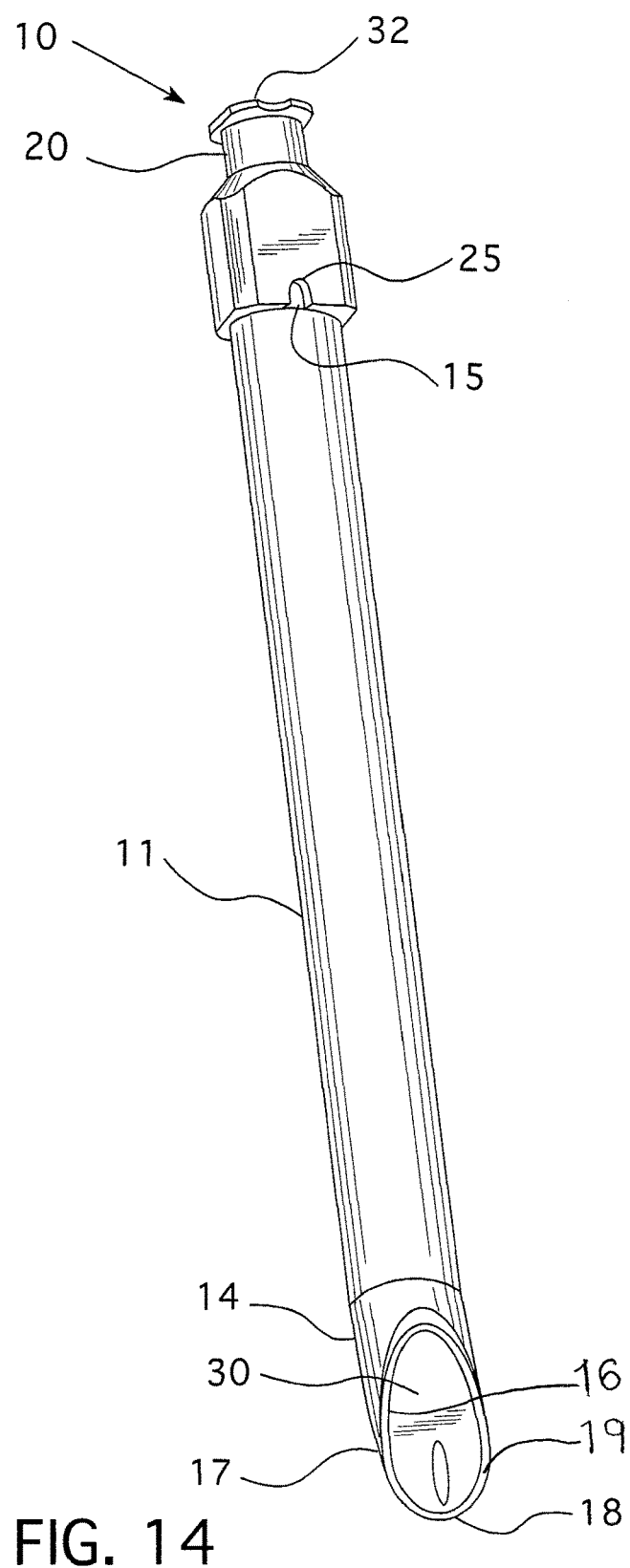
FIG. 14 is a perspective view of the combination shown in FIG. 13.

The syringe needle lumen 21 exits head 22 at the side opening 13 of introducer sleeve needle 11, as best illustrated in FIG. 6, immediately adjacent the tissue piercing tip 18 of introducer sleeve needle 11 whereby the needle assembly 10 illustrated in FIG. 6 may be percutaneously inserted and advanced with tactile feedback into a patient for thereby safely and accurately introducing the distal end 17 of introducer sleeve needle 11 into epidural space. The assembly shown in FIG. 6 thus provides the ability to inform the operator as to the exact location of the point 18 and the point 23 simultaneously which is not possible with the needle assemblies of the prior art.

The hub 20 of syringe needle 12 and the proximal end 15 of introducer sleeve needle 11 are keyed against relative rotation when the hub 12 is fully seated on the proximal end 15 of introducer sleeve needle 11. This keying arrangement is provided by the inter-engagement of alignment notch 24 provided in the bottom of hub 20 and the corresponding alignment protrusion 25. The inter-engagement of protrusion 25 into alignment notch 24 of hub 20 is preferably a snap fit to thereby maintain the two members together in alignment, until such time that they are pulled apart with force.

This epidural needle assembly 10 shown in FIG. 6 thus uniquely permits the loss of resistance technique to be precisely employed when introducing the large bore introducer sleeve needle 11 into the epidural space.

The needle assembly 10 of the present invention may also include a stylet 26 which is a solid rod that is removably insertable in the syringe lumen 21. The stylet 26 is dimensioned to plug the syringe lumen 21 where it exits head 22 whereby debris is prevented from entering the distal end of the syringe lumen. Stylet 26 is provided with a hub 27 at its proximal end which is dimensioned and contoured to seat into syringe needle hub 20 when stylet 26 is fully inserted into the syringe needle lumen 21 whereby lumen exit 28 in head 22 is fully plugged. Thus the distal end 29 of stylet 26 is contoured to mate the surface of syringe needle head 22 at the portion 30 which is exposed by the beveled side opening 16 of introducer needle 11 when stylet 26 is fully seated into syringe needle 12.

Stylet hub 27 and syringe needle hub 20 are keyed against relative rotation when fully seated together by alignment protrusion 31 on hub 27 which projects into alignment notch 32 at the proximal end of syringe hub 20. The fit between alignment protrusion 31 and complementary alignment notch 32 is preferably that of a snap fit to prevent accidental dislodgement therebetween.

The embodiment of the epidural needle assembly 10 of the present invention illustrated in FIGS. 7 through 13, is in all respects identical to that illustrated in the previous embodiment with the exception that the cross section of introducer sleeve needle 11 in the previous embodiment is circular, whereas the cross section of the embodiment illustrated in FIGS. 9 through 13 is oblong. Accordingly, the same elements of this latter embodiment are designated with the identical reference numerals.

The needle assembly of the present invention is applied by first filling the beveled side opening 16 of introducer sleeve needle 11 with the head 22 of syringe needle 12 by inserting syringe needle 12 into the lumen 13 of introducer sleeve needle 11 until hub 24 is fully seated on the distal end 15 of introducer sleeve needle 11. Next, the lumen exit 28 of syringe needle lumen 21 is plugged by inserting solid stylet 26 into lumen 21 of syringe needle 12 to thereby block the entry of debris into syringe lumen exit 21, thereby completing the assembly.

This assembly is then inserted into the skin of the patient at a desired spinal area by percutaneously inserting the point 18 of introducer sleeve needle 11, together with the remainder of the assembly into the skin. Once the skin has been penetrated, stylet 26 is removed from syringe needle lumen 21 and a conventional plunger actuated syringe (not shown) containing non-toxic fluid, such as saline solution or air, is secured in a conventional manner to syringe hub 20.

Then the assembly is advanced through soft tissue layers underlying the skin toward epidural space while applying plunger ejection pressure to the syringe, thereby ejecting fluid under pressure from the syringe needle lumen exit 28 positioned immediately adjacent to the introducer needle tissue piercing point 18, thereby permitting the operator to accurately detect entry of the point 18 of large bore introducer sleeve needle 11 into epidural space with precise tactile feedback to the plunger of the syringe.

With the introducer needle tip 17 being safely introduced into the epidural space, the syringe needle 12 may then be removed from the introducer needle lumen 13 whereby the introducer sleeve needle 11 remains positioned in epidural space for future use, such as insertion of a paddle lead.

Figure 15:
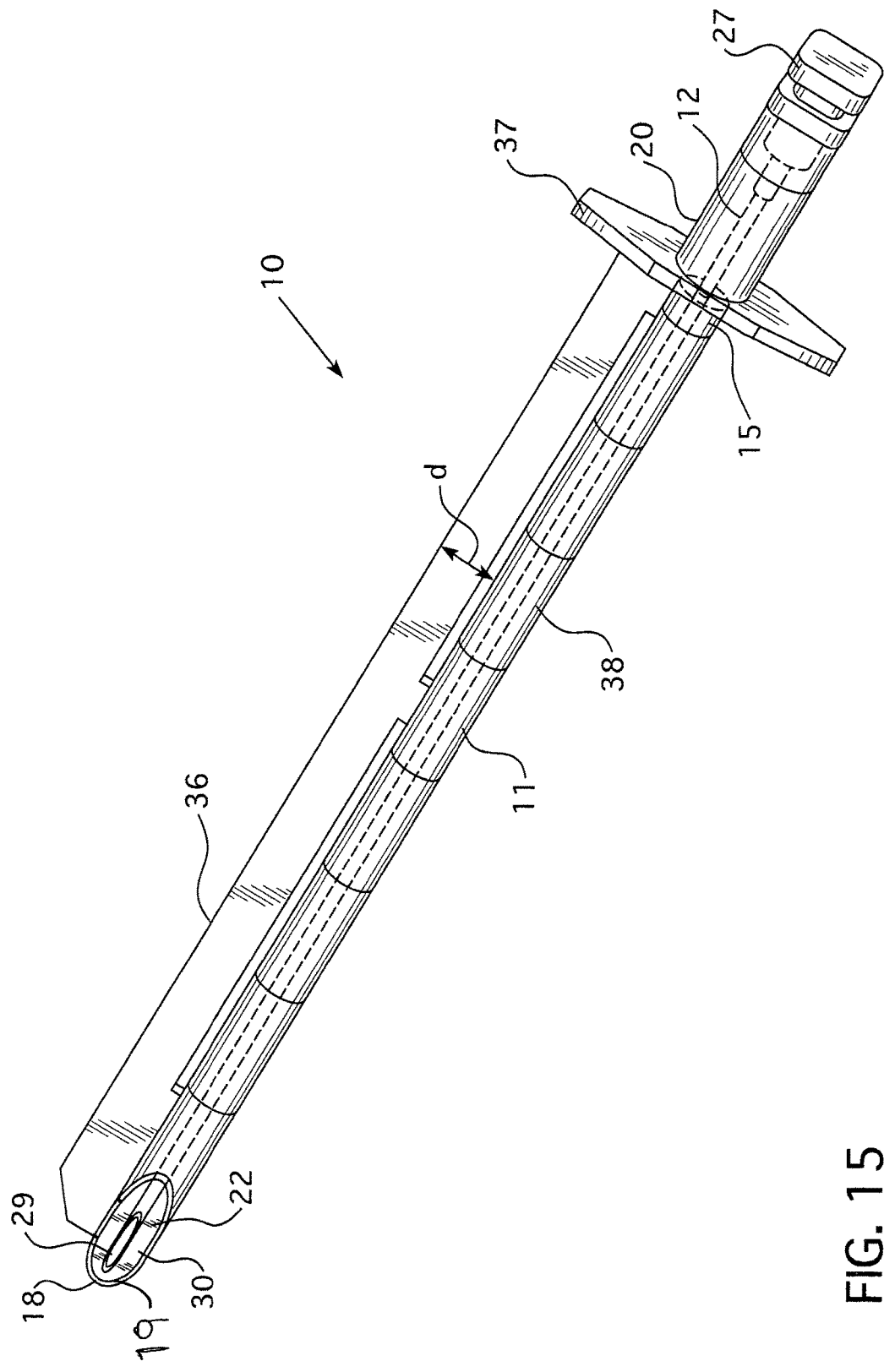
FIG. 15 is a perspective view of another embodiment of the epidural needle assembly of the present invention.
Figure 16:
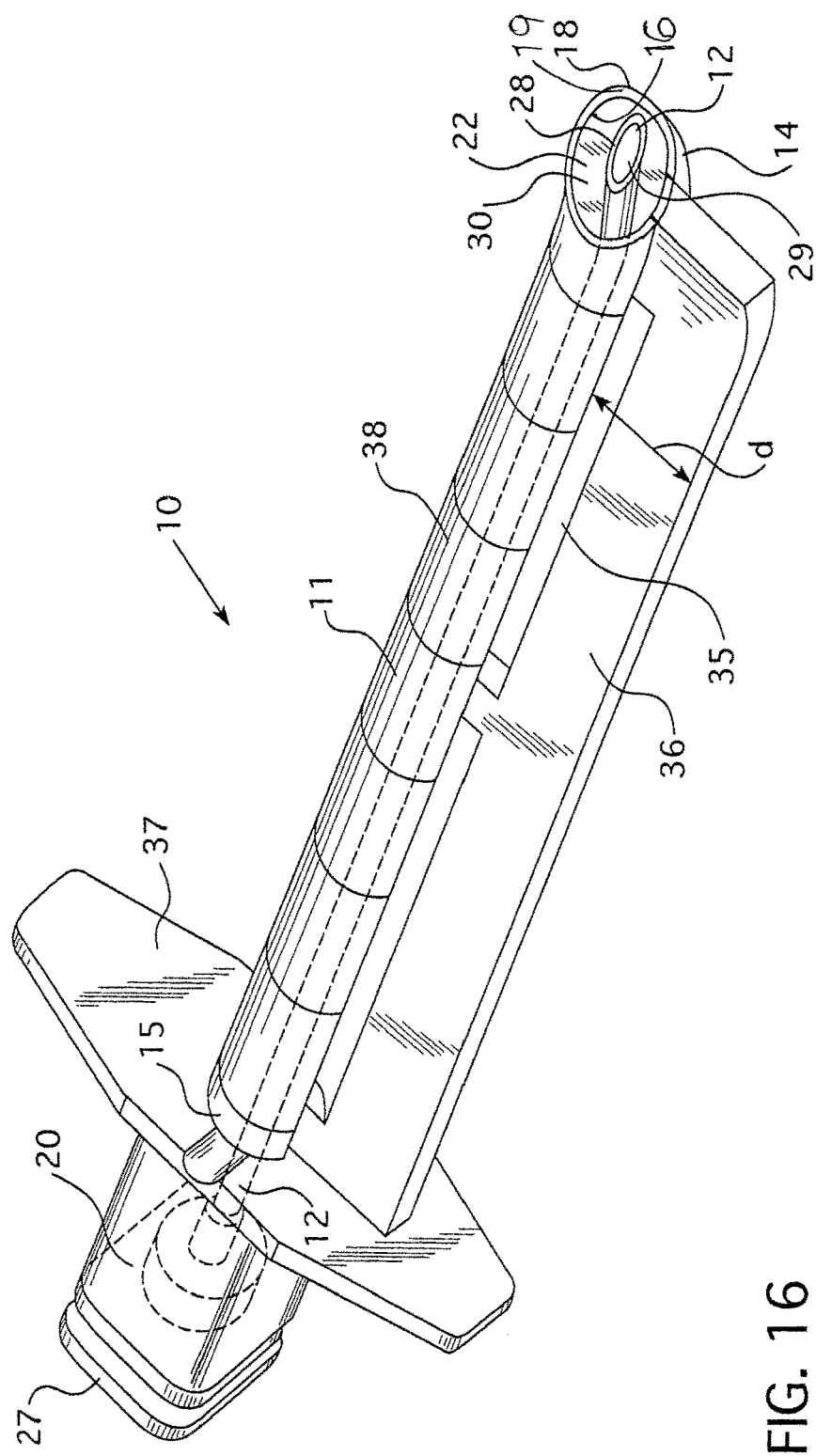
FIG. 16 is a perspective view showing the epidural needle assembly of FIG. 15 as seen from a reverse side perspective.

Referring next to FIGS. 15 and 16, another embodiment of the epidural needle assembly 10 of the present invention is illustrated. This embodiment is in most respects identical to that of the previous embodiments, and accordingly, like elements are designated with the same reference numerals.

In this embodiment, the elongated tubular introducer sleeve needle 11 is provided with a longitudinal side slot 35 that extends the full length of introducer sleeve needle 11. Syringe needle 12 includes a longitudinal wing rib 36 which extends through side slot 35 for a predetermined lateral distance d therebeyond. Accordingly, when the needle assembly 10 is percutaneously introduced into body tissue, the longitudinal wing rib 36 serves to cut, dilate and widen the path of the introducer sleeve needle 11 for later introduction of elements or equipment, such as paddle leads, flat leads or wire leads, which are much broader than permitted with original prior art versions of epidural needle assemblies or introducer sleeve needles.

The wing rib 36 is an integral part of the syringe needle 12 and thus when syringe needle 12 is removed from introducer sleeve needle 11, wing rib 36 is also removed as an integral part thereby leaving a widened path in the tissue adjacent slot 35 of introducer sleeve needle 11, which remains imbedded. Accordingly, a much wider than normal lead element may be inserted through the introducer sleeve 11 into epidural space. The wide lead passes not only through the lumen of introducer sleeve needle 11 but also portions thereof extending through slot 35 and through the dilated tissue passage produced by wing rib 36. Accordingly, introduction of much wider lead equipment or elements is permitted. For example, a 10 mm wide lead element may be inserted as compared to a 4 mm lead element possible with the introducer needles of the prior art, or the simultaneous passage of multiple leads side by side.

Figure 3:
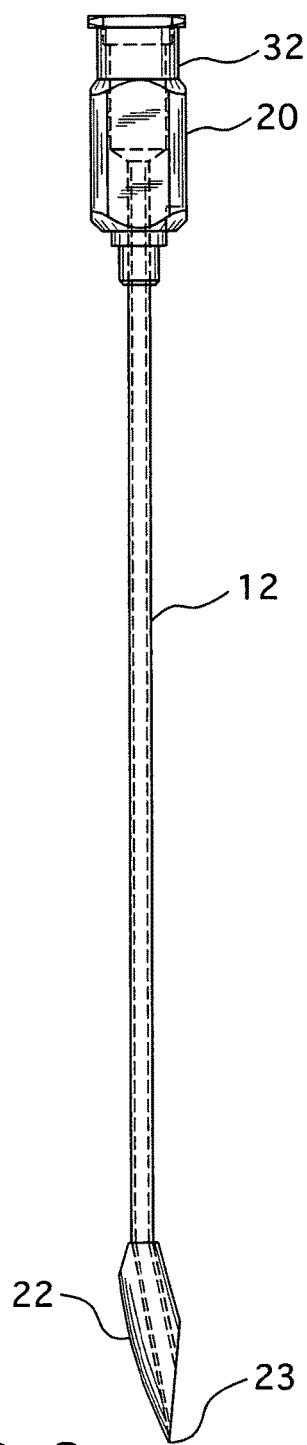
FIG. 3 is a view is side elevation of a syringe needle utilized in the epidermal needle assembly of the present invention.
Figure 4:
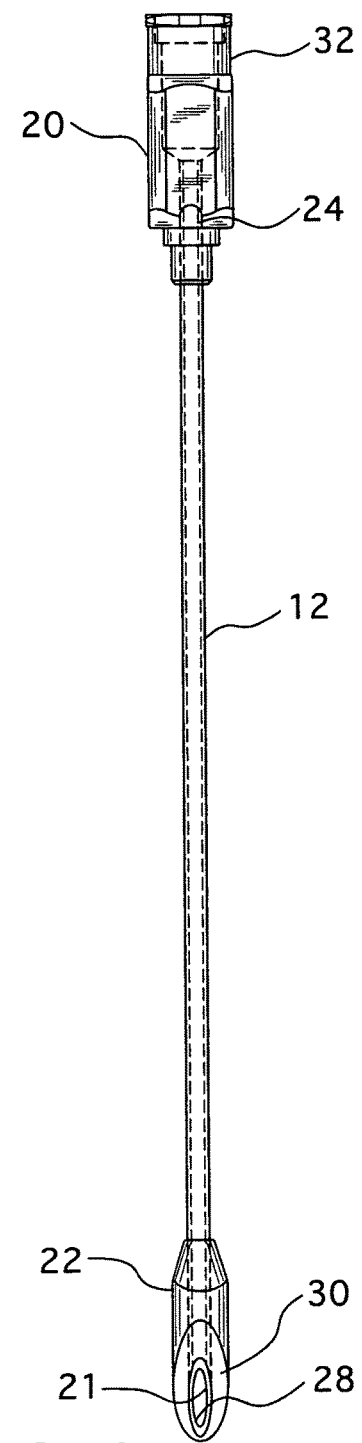
FIG. 4 is a view in front elevation of the syringe needle shown in FIG. 3.
Figure 5:
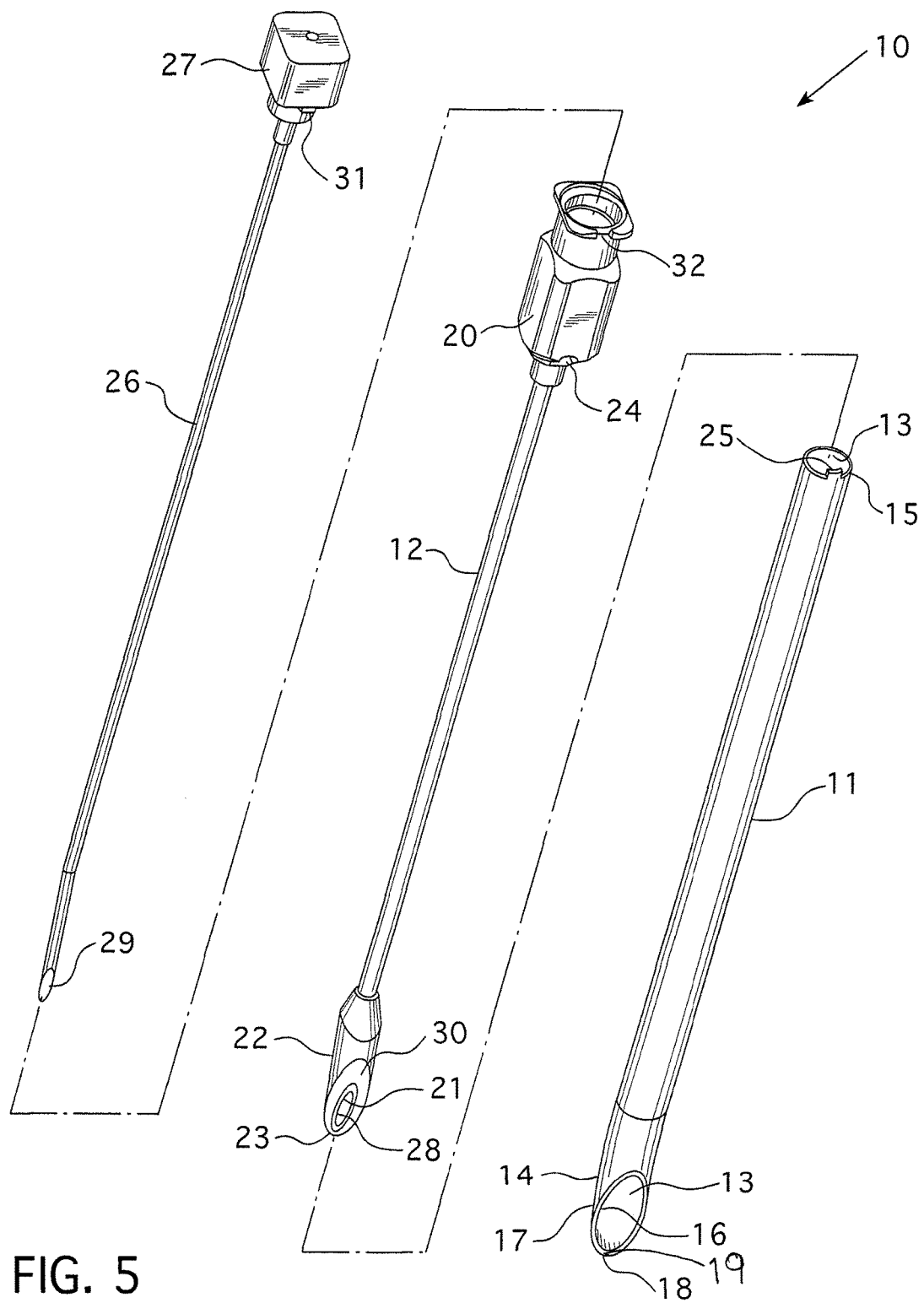
FIG. 5 is an exploded view of the stylet, syringe needle and introducer sleeve needle shown in perspective, which are combined to provide the epidural needle assembly of the present invention.

The longitudinal wing rib 36 is contoured and specifically matched and mated to fit the length of the apparatus in FIGS. 3 and 4. In this way, the cutting edge of the longitudinal wing rib is positioned to navigate through ligaments (and other subcutaneous tissue) en route to the epidural space at the same exact time as the exit 28 of needle 12 is traversing through said tissue. Thus, the operator will know where the wing rib is in relation to the tubular introducer sleeve needle 11 at all times.

Finger grip wings 37 are provided on the upper end of syringe needle 22 to facilitate handling. Finger grip wings 37, enlarged head 22, wing rib 36 and the upper end 15 of syringe needle 12 are integrally molded of transparent medical blue polypropylene. However, wing rib 36 is preferably constructed of surgical stainless steel with cutting leading and side edges to cut tissue.

Introducer sleeve needle 11 is provided with 1 cm depth markings 38 to aid the operator in accessing how deep beneath the tissue the tip 18 is located.

I claim:

1. An epidural needle assembly for safely introducing an introducer needle into an epidural space of a patient spinal column, comprising:
    an elongated tubular introducer sleeve needle having a lumen extending from its distal tip to its proximal end with a beveled side opening at its distal tip providing a tissue piercing point;
    a syringe needle having a proximal end and a distal end and an internal lumen of predetermined cross section continuously extending therethrough, a syringe hub secured to said proximal end of the syringe needle and a head secured to said distal end of the syringe needle; wherein:
    said head of said syringe needle is an enlarged head secured to said distal end and said syringe needle is dimensioned and contoured to be received in said lumen of said introducer sleeve needle with said syringe hub of said syringe needle releaseably seated with said proximal end of said introducer sleeve needle and with said enlarged head of the syringe needle filling and terminating at said beveled side opening of said introducer sleeve needle when said syringe hub is fully seated to the proximal end of said introducer sleeve needle;
    said internal lumen of the syringe needle exiting said enlarged head at said filled beveled side opening immediately adjacent said tissue piercing point of said introducer sleeve needle, whereby said needle assembly is percutaneously inserted and advanced with loss of resistance tactile feedback into tissue of a patient for thereby safely and accurately introducing a distal end of said introducer sleeve needle into the epidural space of the patient spinal column.

2. The needle assembly of claim 1, wherein said internal lumen of the syringe needle is in the range of 14 to 18 gauge.

3. The needle assembly of claim 2, including a syringe secured to said syringe hub.

4. The needle assembly of claim 1, wherein said distal tip of said introducer sleeve needle is curved in the direction of said beveled side opening.

5. The needle assembly of claim 4, wherein a cross-section of said introducer sleeve needle is circular.

6. The needle assembly of claim 4, wherein a cross-section of said introducer sleeve needle is oblong.

7. The needle assembly of claim 1, wherein said hub of said syringe needle and said proximal end of said introducer sleeve needle are keyed against relative rotation when said hub is fully seated on said proximal end of said introducer sleeve needle.

8. The needle assembly of claim 1, including a stylet removably insertable in said internal lumen of the syringe needle and dimensioned to plug said internal lumen whereby debris is prevented from entering a distal end of the internal lumen of the syringe needle.

9. The needle assembly of claim 8, wherein said stylet includes a hub at its proximal end which is dimensioned and contoured to seat into said syringe hub when said stylet is fully inserted into said syringe needle lumen whereby a distal lumen exit in said head of the syringe needle is plugged.

10. The needle assembly of claim 9, wherein a distal tip of said stylet when fully seated is contoured to mate a surface of said enlarged head of the syringe needle which is exposed by said introducer sleeve needle beveled side opening.

11. The needle assembly of claim 9, wherein the hub of the stylet and said syringe hub are keyed against relative rotation when fully seated together.

12. The needle assembly of claim 1, said introducer sleeve needle having a longitudinal side slot, said syringe needle including a longitudinal wing rib which extends through said side slot for a predetermined lateral distance therebeyond whereby a path made by said introducer sleeve needle is dilated and thereby widened for later introduction of wide lead elements.

13. The needle assembly of claim 12, wherein said introducer sleeve needle and said syringe needle are stainless steel and said wing rib is a rigid plastic secured to said syringe needle.

14. The needle assembly of claim 13, wherein said rigid plastic of said wing rib is polypropylene.

15. The needle assembly of claim 1, said introducer sleeve needle includes depth markings on an exterior thereof for assessing depth of penetration.

16. The needle assembly of claim 15, wherein said depth markings are in centimeter increments.

\* \* \* \* \*